(12) United States Patent
Arnin et al.

(10) Patent No.: US 7,604,652 B2
(45) Date of Patent: Oct. 20, 2009

(54) SPINAL PROSTHESIS

(75) Inventors: Uri Arnin, Kiryat Tivon (IL); Yuri Sudin, Lod (IL)

(73) Assignee: Impliant Ltd., Netanya (IL)

( * ) Notice: Subject to any disclaimer, the term of this patent is extended or adjusted under 35 U.S.C. 154(b) by 364 days.

(21) Appl. No.: 11/349,956

(22) Filed: Feb. 9, 2006

(65) Prior Publication Data
US 2007/0093816 A1  Apr. 26, 2007

Related U.S. Application Data

(60) Provisional application No. 60/724,876, filed on Oct. 11, 2005, provisional application No. 60/754,296, filed on Dec. 29, 2005.

(51) Int. Cl.
*A61B 17/70* (2006.01)
(52) U.S. Cl. ..................................................... 606/249
(58) Field of Classification Search .................. 606/61, 606/250–253, 257, 259, 260, 246, 249; 623/17.14
See application file for complete search history.

(56) References Cited

U.S. PATENT DOCUMENTS

| | | | |
|---|---|---|---|
| 4,836,196 A | | 6/1989 | Park et al. |
| 5,562,737 A | * | 10/1996 | Graf ........................ 623/17.14 |
| 6,875,211 B2 | * | 4/2005 | Nichols et al. ................ 606/61 |
| 7,291,150 B2 | * | 11/2007 | Graf ........................ 606/86 A |
| 7,294,129 B2 | * | 11/2007 | Hawkins et al. ........... 606/86 A |
| 2006/0217719 A1 | * | 9/2006 | Albert et al. .................. 606/61 |
| 2007/0088358 A1 | * | 4/2007 | Yuan et al. .................... 606/61 |

FOREIGN PATENT DOCUMENTS

| | | |
|---|---|---|
| DE | 2834891 | 1/1980 |
| EP | 0340160 | 11/1989 |
| EP | 1364621 | 11/2003 |

* cited by examiner

*Primary Examiner*—Eduardo C Robert
*Assistant Examiner*—Ellen Rust
(74) *Attorney, Agent, or Firm*—Dekel Patent Ltd.; David Klein

(57) ABSTRACT

A spinal prosthesis including a first spinal attachment member attachable to a first posterior portion of a spinal structure, a second spinal attachment member attachable to a second posterior portion of the spinal structure, the first and second posterior portions being adjacent superiorly-inferiorly to one another, and a connector element attached to the first spinal attachment member, wherein the second spinal attachment member includes an interface portion that passes through an elongate aperture formed in the connector element so as to permit rotational and translational movement of the second spinal attachment member with respect to the connector element.

18 Claims, 4 Drawing Sheets

SPINAL PROSTHESIS

CROSS-REFERENCE TO RELATED APPLICATIONS

This application claims priority under 35 USC §119 to U.S. Provisional Patent Application, Ser. No. 60/724,876, filed Oct. 11, 2005, and U.S. Provisional Patent Application, Ser. No. 60/754,296, filed Dec. 29, 2005, both of which are incorporated herein by reference.

FIELD OF THE INVENTION

The present invention is generally related to apparatus and methods for spinal prostheses.

BACKGROUND OF THE INVENTION

Spinal stenosis, as well as spondylosis, spondylolisthesis, osteoarthritis and other degenerative phenomena may cause back and leg pain. Such phenomena may be caused by a narrowing of the spinal canal by a variety of causes that result in the pinching of the spinal cord and/or nerves in the spine. Fusion of two or more adjacent vertebrae has been to alleviate such back and leg pain. However, fusion of vertebrae can be disfavored because fusion tends to cause degenerative phenomena in the fused vertebrae to migrate to adjacent vertebral components that have not been fused.

SUMMARY OF THE INVENTION

The present invention seeks to provide a novel spinal prosthesis, as is described more in detail hereinbelow. The prostheses disclosed herein are particularly advantageous for the posterior portion of the spine, but the invention is not limited to the posterior portion of the spine.

There is thus provided in accordance with an embodiment of the present invention a spinal prosthesis including a first spinal attachment member attachable to a first posterior portion of a spinal structure, a second spinal attachment member attachable to a second posterior portion of the spinal structure, the first and second posterior portions being adjacent superiorly-inferiorly to one another, and a connector element attached to the first spinal attachment member, wherein the second spinal attachment member includes an interface portion that passes through an elongate aperture formed in the connector element so as to permit rotational and translational movement of the second spinal attachment member with respect to the connector element.

The spinal prosthesis can include one or more of the following features. For example, the interface portion may pass through the elongate aperture so as to permit rotational movement of the second spinal attachment member with respect to the connector element about at least two different rotational axes (which may be mutually orthogonal). The first spinal attachment member may be rotatably received in a bore formed in the connector element. The elongate aperture may define limits of movement of the second spinal attachment member with respect to the connector element. The elongate aperture may be elongate along a first axis and have end faces that face in opposite directions along a second axis, and the interface portion may have abutments spaced from the end faces of the elongate aperture, wherein the abutments define limits of movement of the interface portion. The end faces and the abutments may have curved contours that mate with each other. For example, the end faces may have concave contours and the abutments may have convex contours. The connector element and the interface portion may have different hardness.

The first and second spinal attachment members may include elongate members with pedicle screws near ends thereof. In accordance with a non-limiting embodiment of the invention, the elongate members of the first spinal attachment member are not collinear with the connector element and extend away from the connector element at an angle different than that of the elongate members of the second spinal attachment member extending from the connector element.

DETAILED DESCRIPTION OF EMBODIMENTS

Figure 1A:
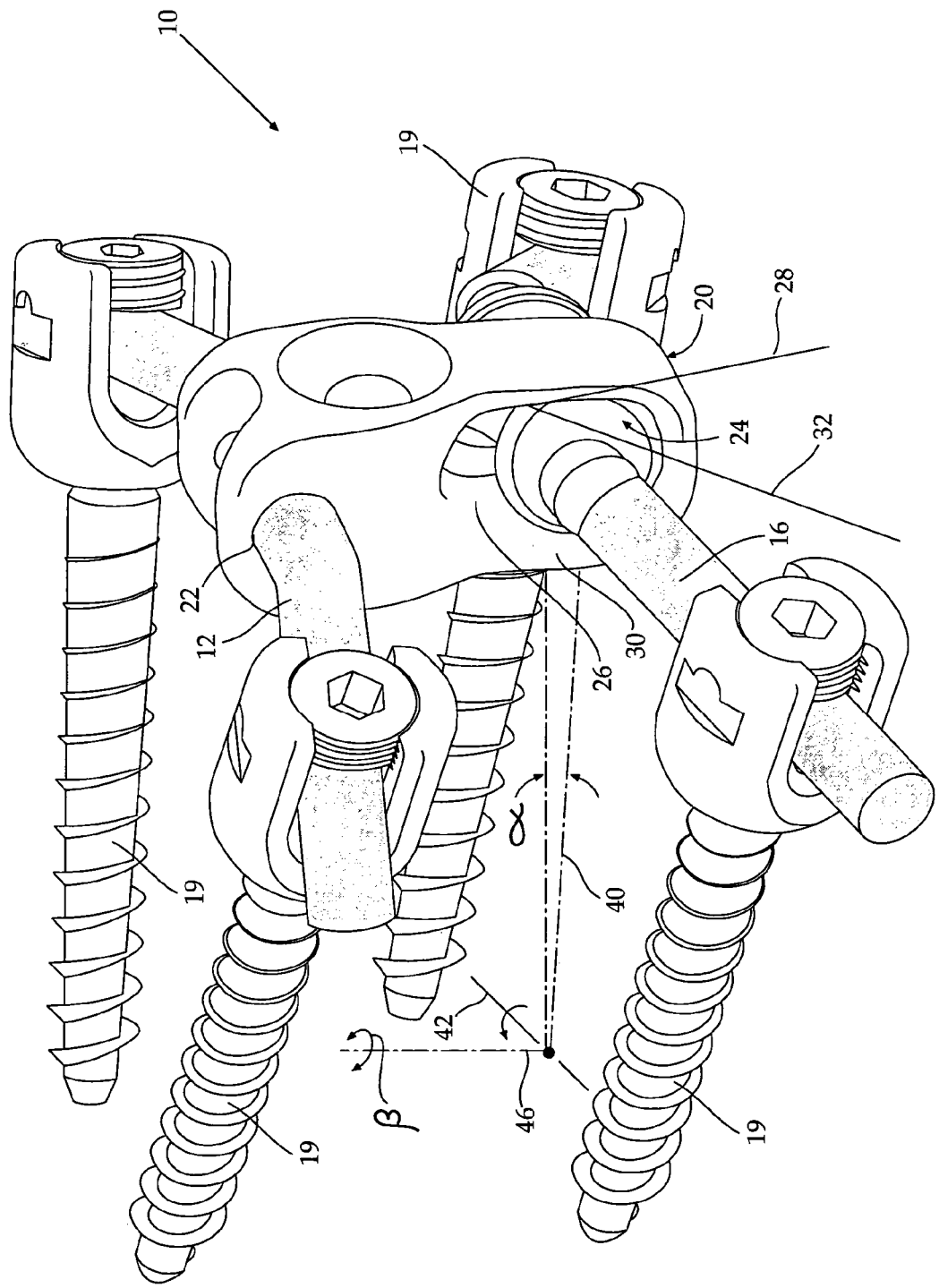
FIGS. 1A and 1B are simplified pictorial illustrations of a spinal prosthesis, constructed in accordance with an embodiment of the present invention, in two different rotational orientations about a first rotational axis.
Figure 1B:
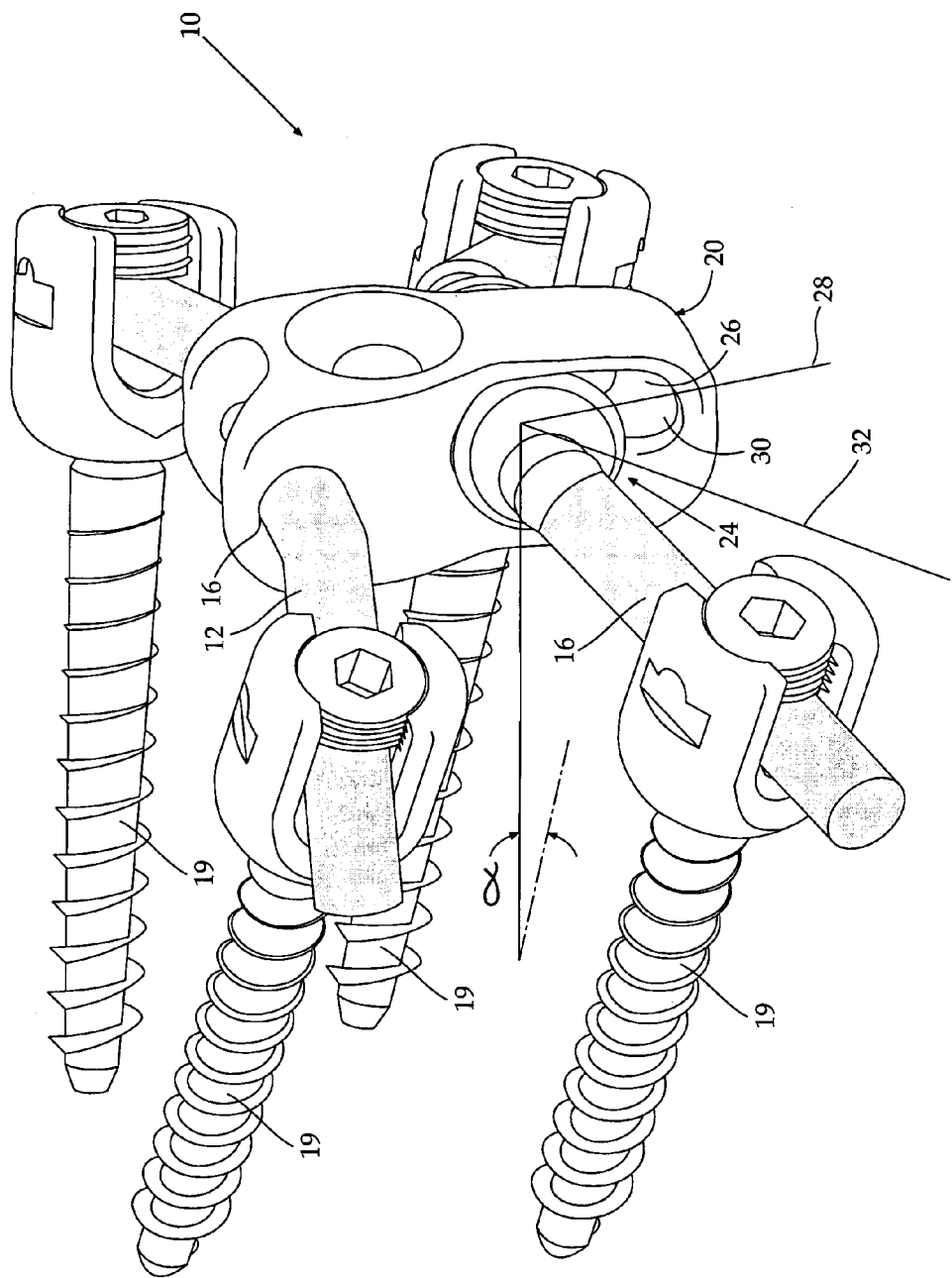
Figure 2:
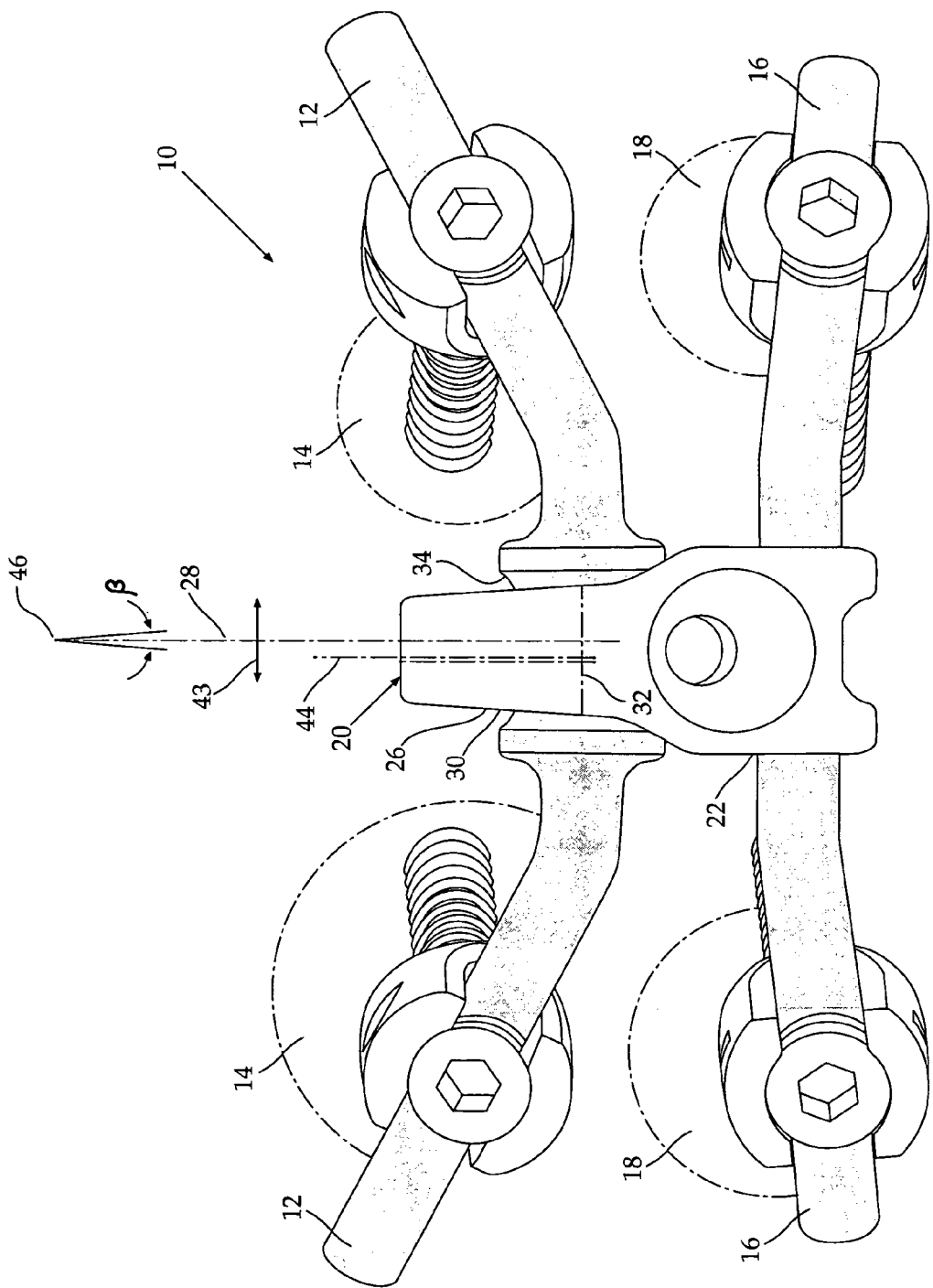
FIG. 2 is a pictorial illustration of the spinal prosthesis of FIGS. 1A and 1B, showing rotational movement about a second rotational axis.

Reference is now made to FIGS. 1A, 1B and 2, which illustrate a spinal prosthesis 10, constructed and operative in accordance with an embodiment of the present invention.

Spinal prosthesis 10 may include a first spinal attachment member 12 attachable to a first posterior portion 14 (FIG. 2) of a spinal structure (e.g., the pedicles of the L4 vertebra, shown simplistically in broken lines). Spinal prosthesis 10 may further include second spinal attachment member 16 attachable to a second posterior portion 18 (FIG. 2) of the spinal structure (e.g., the pedicles of the L5 vertebra, shown simplistically in broken lines). The first and second posterior portions 14 and 18 may be adjacent superiorly-inferiorly to one another (as in the example given above, L4 and L5). Thus, first and second spinal attachment members 12 and 16 may serve as cephalad and caudal attachment members, respectively.

In the non-limiting illustrated embodiment, first and second spinal attachment members 12 and 16 include elongate members (e.g., rods of any cross-sectional shape, such as circular or prismatic) that can be connected to the spinal structure with pedicle screws 19 (e.g., with polyaxial heads). A laminectomy including the removal of the spinous process between the adjacent vertebrae may be performed prior to attachment of the pedicle screws 19 to adjacent vertebrae such as, for example, L4 and L5 of the lumbar vertebrae.

A connector element 20 may be provided for assembling with the first and second spinal attachment members 12 and 16, respectively. Connector element 20 may be formed with a bore 22 into which first spinal attachment member 12 may be fixedly attached. Second spinal attachment member 16 may include an interface portion 24 that passes through an elongate aperture 26 formed in connector element 20. Second spinal attachment member 16 can rotate and translate with respect to connector element 20, as will be explained hereinbelow. The interface portion 24 may be rotatingly assembled on second spinal attachment member 16, and thus may act as a roller bearing.

The elongate aperture 26 may be elongate along a first axis 28 and may have end faces 30 that face in opposite directions along a second axis 32, which may be orthogonal to axis 28. Interface portion 24 may have abutments 34 spaced from the end faces 30 of elongate aperture 26. End faces 30 and abutments 34 may have curved contours that mate with each other. For example, end faces 30 may have concave contours (as seen best in FIGS. 1A and 1B) and abutments 34 may have convex contours (as seen best in FIG. 2).

First and second spinal attachment members 12 and 16 and connecting element 20 may be fashioned from any suitable medically safe material, such as but not limited to, cobalt chrome, stainless steel, or titanium. Interface portion 24 may be made of these materials, or alternatively may be made of an elastomeric material, such as polyurethane or natural or synthetic rubber. Thus, connector element 20 and interface portion 24 may have different hardness.

As seen in the non-limiting embodiment illustrated in FIGS. 1A and 1B, the elongate members of the first spinal attachment member 12 are not collinear with connector element 20 and extend away from connector element 20 at an angle different than that of the elongate members of the second spinal attachment member 16 extending from connector element 20.

FIG. 1A illustrates spinal prosthesis 10 in an orientation wherein interface portion 24 is at the bottom ("bottom" in the sense of the drawing) of elongate aperture 26 along a reference axis 40. Due to the elongate shape of aperture 26, interface portion 24 and connector element 20 are free to move relative to one another so that interface portion 24 is situated at the top ("top" in the sense of the drawing) of elongate aperture 26, as seen in FIG. 1B. By comparison of the two positions shown in FIGS. 1A and 1B, it is readily seen that there has been rotational movement (through angle a) of second spinal attachment member 16 with respect to connector element 20 about a rotational axis 42, which may be orthogonal to reference axis 40. The elongate aperture 26 defines the limits of rotational movement about rotational axis 42.

Referring now to FIG. 2, it may be seen that translatory movement of second spinal attachment member 16 with respect to connector element 20 is possible. This is because the abutments 34 are preferably not tightly received in end faces 30 but rather permit side-to-side motion (in the sense of FIG. 2), as indicated by arrows 43, such as from axis 28 to another reference axis 44. The abutments 34 define the limits of the translational movement. Moreover, due to the freedom of interface portion 24 to move in elongate aperture 26, additional rotational movement of second spinal attachment member 16 with respect to connector element 20 is possible about a second rotational axis 46 (through angle β), which may be orthogonal to rotational axis 42. Interface portion 24 acting as a roller bearing also contributes to the freedom of movement. Connector element 20 may thus serve as a single central articulating element positioned at a central portion of first and second spinal attachment members 12 and 16.

Figure 3A:
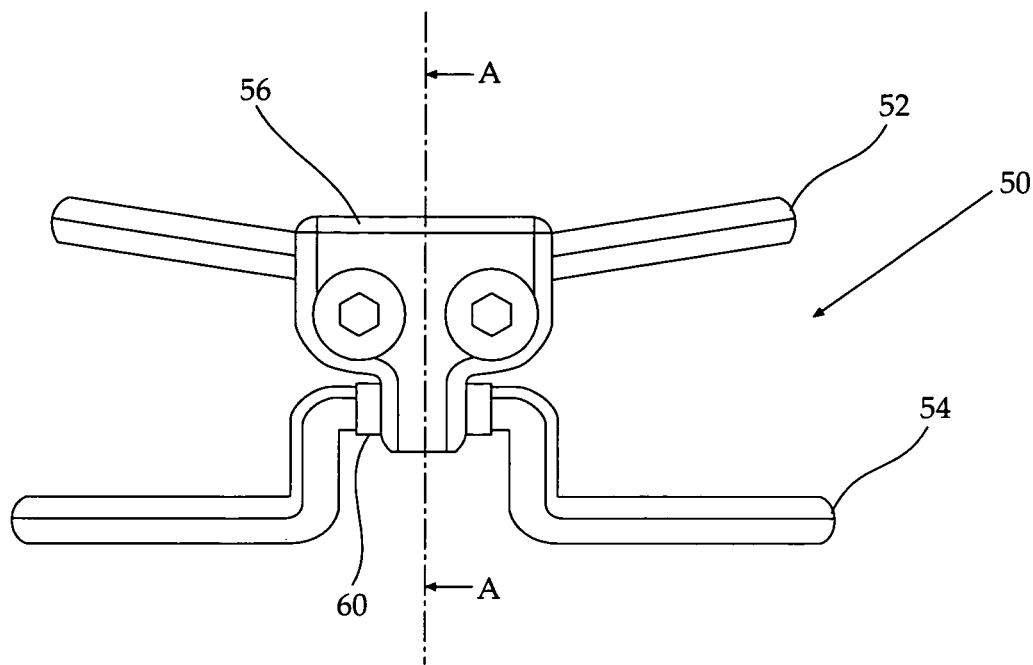
FIGS. 3A and 3B are simplified front and partially sectional side view illustrations, respectively, of a spinal prosthesis, constructed and operative in accordance with another embodiment of the present invention.
Figure 3B:
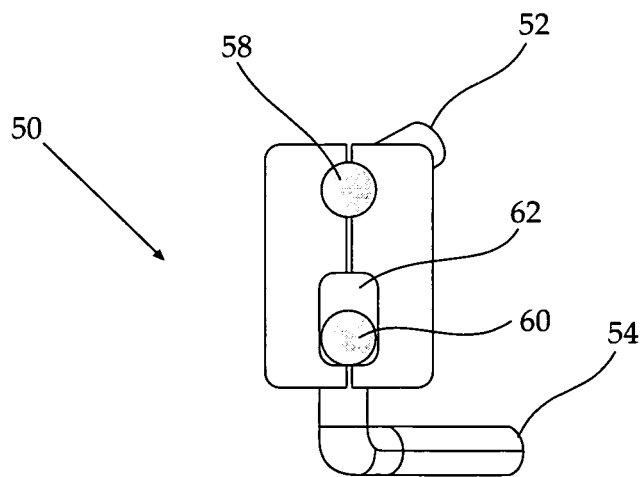

Reference is now made to FIGS. 3A and 3B, which illustrate a spinal prosthesis 50, constructed and operative in accordance with another embodiment of the present invention. Similar to spinal prosthesis 10, spinal prosthesis 50 may include a first spinal attachment member 52 attachable to a first posterior portion of a spinal structure (e.g., the pedicles of the L4 vertebra, not shown in FIGS. 3A and 3B, but as shown in FIG. 2), and a second spinal attachment member 54 attachable to a second posterior portion of the spinal structure (e.g., the pedicles of the L5 vertebra, not shown). As above, first and second spinal attachment members 52 and 54 may serve as cephalad and caudal attachment members, respectively. The second spinal attachment member 54 may have a bent configuration as shown in FIG. 3A.

A connector element 56 may be provided for assembling with the first and second spinal attachment members 52 and 54, respectively. Connector element 56 may be formed with a bore 58 through which first spinal attachment member 52 passes. First spinal attachment member 52 can rotate about the center of bore 58. Second spinal attachment member 54 may include an interface portion 60 that passes through an elongate aperture 62 formed in connector element 56. Second spinal attachment member 54 can rotate and translate, resulting in relative freedom of movement in all directions, with respect to connector element 56, as explained similarly hereinabove for the embodiments of FIGS. 1A and 1B. The interface portion 60 may be rotatingly assembled on second spinal attachment member 54, and thus may act as a roller bearing. As similarly above, connector element 56 may serve as a single central articulating element positioned at a central portion of first and second spinal attachment members 52 and 54.

Spinal prosthesis 10 or 50 may be constructed of several parts assembled prior to or during the surgical procedure, or may be a unitary implant consisting of all elements mentioned above. An advantage of a unitary implant is that it enables a relatively rapid procedure and does not require accurate adjustments in the operating room, which is most advantageous for the implant recipient. A typical procedure may consist of a posterior incision into the area adjacent to the affected vertebrae, a laminectomy, insertion of pedicle screws (or even reuse of pedicle screws from another procedure such as fusion) and the implantation of spinal prosthesis 10 or 50 by the pedicle screws to pedicles or other available bone structure. The freedom of movement of second spinal attachment member 16 or 54 with respect to connector element 20 or 56 may simplify the implantation procedure, and may also enable a predetermined range of movement of the two adjacent vertebrae in relationship to each other, in contrast to spinal fusion, for example.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. A spinal prosthesis comprising:
   a first spinal attachment member attachable to a first posterior portion of a spinal structure;
   a second spinal attachment member attachable to a second posterior portion of the spinal structure, said first and second posterior portions being adjacent superiorly-inferiorly to one another; and
   a connector element attached to said first spinal attachment member, wherein an interface portion is rotatingly assembled on said second spinal attachment member and acts as a roller bearing therefor, and wherein said interface portion passes through an elongate aperture formed in said connector element so as to permit rotational and translational movement of said second spinal attachment member with respect to said connector element, wherein said rotational movement of said second spinal attachment member with respect to said connector element is about at least two different rotational axes, and wherein said second spinal attachment member comprises elongate members that extend outwards from opposite sides of said interface portion, wherein said elongate aperture is elongate along a first axis and has end faces that face in opposite directions along a second axis, and said interface portion has abutments spaced from the end faces of said elongate aperture, wherein said abutments define limits of movement of said interface portion.

2. The spinal prosthesis according to claim 1, wherein said rotational axes are mutually orthogonal axes.

3. The spinal prosthesis according to claim 1, wherein said elongate aperture defines limits of movement of said second spinal attachment member with respect to said connector element.

4. The spinal prosthesis according to claim 1, wherein said end faces and said abutments have curved contours that mate with each other.

5. The spinal prosthesis according to claim 1, wherein said end faces have concave contours and said abutments have convex contours.

6. The spinal prosthesis according to claim 1, wherein said connector element and said interface portion have a different hardness.

7. The spinal prosthesis according to claim 1, wherein said first and second spinal attachment members comprise elongate members with pedicle screws near ends thereof.

8. The spinal prosthesis according to claim 7, wherein the elongate members of said first spinal attachment member are not collinear with said connector element and extend away from said connector element at an angle different than that of the elongate members of said second spinal attachment member extending from said connector element.

9. The spinal prosthesis according to claim 1, wherein said elongate members of said second spinal attachment member are attached to polyaxial heads of pedicle screws.

10. A spinal prosthesis comprising:
  a first spinal attachment member attachable to a first posterior portion of a spinal structure;
  a second spinal attachment member attachable to a second posterior portion of the spinal structure, said first and second posterior portions being adjacent superiorly-inferiorly to one another; and
  a connector element attached to said first spinal attachment member, wherein an interface portion is rotatingly assembled on said second spinal attachment member and acts as a roller bearing therefor, and wherein said interface portion passes through an elongate aperture formed in said connector element so as to permit rotational and translational movement of said second spinal attachment member with respect to said connector element, wherein said rotational movement of said second spinal attachment member with respect to said connector element is about at least two different rotational axes, and wherein said second spinal attachment member comprises elongate members that extend outwards from opposite sides of said interface portion, wherein said connector element comprises a single central articulating element positioned at a central portion of said first and second spinal attachment members.

11. The spinal prosthesis according to claim 10, wherein said rotational axes are mutually orthogonal axes.

12. The spinal prosthesis according to claim 10, wherein said elongate aperture defines limits of movement of said second spinal attachment member with respect to said connector element.

13. The spinal prosthesis according to claim 10, wherein said end faces and said abutments have curved contours that mate with each other.

14. The spinal prosthesis according to claim 10, wherein said end faces have concave contours and said abutments have convex contours.

15. The spinal prosthesis according to claim 10, wherein said connector element and said interface portion have a different hardness.

16. The spinal prosthesis according to claim 10, wherein said first and second spinal attachment members comprise elongate members with pedicle screws near ends thereof.

17. The spinal prosthesis according to claim 16, wherein the elongate members of said first spinal attachment member are not collinear with said connector element and extend away from said connector element at an angle different than that of the elongate members of said second spinal attachment member extending from said connector element.

18. The spinal prosthesis according to claim 10, wherein said elongate members of said second spinal attachment member are attached to polyaxial heads of pedicle screws.

* * * * *